(12) United States Patent  (10) Patent No.: US 11,101,032 B2
Kohle et al.  (45) Date of Patent: Aug. 24, 2021

(54) SEARCHING A MEDICAL REFERENCE IMAGE

(71) Applicant: Siemens Healthcare GmbH, Erlangen (DE)

(72) Inventors: Sven Kohle, Erlangen (DE); Christian Tietjen, Fuerth (DE); Gerardo Hermosillo Valadez, West Chester, PA (US); Shu Liao, Chester Springs, PA (US); Felix Ritter, Bremen (DE); Jan Kretschmer, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 18 days.

(21) Appl. No.: 16/533,998

(22) Filed: Aug. 7, 2019

(65) Prior Publication Data

US 2020/0058390 A1  Feb. 20, 2020

(30) Foreign Application Priority Data

Aug. 15, 2018  (EP) .................................... 18189090

(51) Int. Cl.
*G06K 9/62*  (2006.01)
*G16H 30/40*  (2018.01)
(Continued)

(52) U.S. Cl.
CPC .............. *G16H 30/40* (2018.01); *G06K 9/40* (2013.01); *G06K 9/6202* (2013.01);
(Continued)

(58) Field of Classification Search
CPC ............................. G16H 30/40; G06K 9/6202
See application file for complete search history.

(56) References Cited

U.S. PATENT DOCUMENTS 9,798,612 B1  10/2017 Foerster et al.
2003/0013951 A1*  1/2003 Stefanescu ............. G16H 50/50
600/407
(Continued)

FOREIGN PATENT DOCUMENTS

EP  3537454 A1  9/2019

OTHER PUBLICATIONS

European Search Report with Application No. 18189090.6 dated Feb. 20, 2019.
(Continued)

*Primary Examiner* — Tuan H Nguyen
(74) *Attorney, Agent, or Firm* — Harness, Dickey & Pierce, P.L.C.

(57) ABSTRACT

A method and system are for identification of at least one medical reference image. An embodiment of the method includes providing a medical representation image based on a current examination image depicting a body part of a first patient; defining a region of interest in the medical representation image; generating a feature signature, at least for the region of interest; comparing the medical representation image with a plurality of medical images of at least one second patient stored in a medical image database, based on the feature signature generated; and identifying at least one medical image in the medical image database as the at least one medical reference image, the at least one medical reference image providing a similarity degree to the medical representation image above a threshold. In an embodiment, the generating is performed using a trained machine-learning algorithm.

25 Claims, 3 Drawing Sheets

(51) Int. Cl.
  *G16H 50/20* (2018.01)
  *G06K 9/40* (2006.01)
(52) U.S. Cl.
  CPC ........... *G06K 9/6215* (2013.01); *G16H 50/20* (2018.01); *G06K 2209/05* (2013.01)

(56) References Cited

U.S. PATENT DOCUMENTS

2016/0300120 A1  10/2016  Haas et al.
2018/0089840 A1*  3/2018  Yan .................... G06K 9/00288

OTHER PUBLICATIONS

Communication Pursuant to article 94(3) EPC dated Feb. 1, 2021 in European Application No. 18189090.6.

* cited by examiner

SEARCHING A MEDICAL REFERENCE IMAGE

PRIORITY STATEMENT

The present application hereby claims priority under 35 U.S.C. § 119 to European patent application number EP 18189090.6 filed Aug. 15, 2018, the entire contents of which are hereby incorporated herein by reference.

FIELD

Embodiments of the invention generally relate to a method and system for identification of at least one medical reference image.

BACKGROUND

In daily work, radiologists are often confronted with medical images depicting peculiar image patterns according to incidental findings which are hard to classify at first glance. Still, these images need documentation in the corresponding radiological report. Accordingly, incidental findings are described by their imaging characteristics, preferably, using free-text form without deduction of a specific diagnosis.

If possible, radiologists may manually screen clinical textbooks, imaging atlases or obtain a second, rather expert opinion to classify the incidental findings. Then, appropriate differential diagnosis may be applied. This procedure is independent of the technical standard present in a radiology, thus independent on film based reading on light boxes, reading in digital PACS viewers or reading with advanced visualization applications/stations like e.g. Syngo.via®. The amount of clinical studies, literature and/or clinical guidelines for differential diagnosis is huge and as such impossible to be known for individual radiologists. Furthermore, radiologists often work under severe time constraints.

Generally, image search portals are available and well known, e.g. Google Image Search. Individual images may be uploaded and compared to images stored publically in the internet. While these portals are generally unsuited to find diseases based on a given image pattern of a medical image in question (e.g. due to the fact that known software solutions do not or not compatibly offer the possibility to grab a region of interest (ROI) to send it to the portal), this approach would also require presence of and tight integration into radiology reading hard- and software environment. Thus, only selected users with high-end equipment could at all benefit from image search portals for radiological purposes.

Apart from that, it is well known that taking digital photographs from monitors and/or displays as e.g. used in radiology for image reading introduces severe image artefacts and/or distortions which hinder the application of generally known image pattern search based on digital photographs in radiology. Still, many radiologists use their smartphones to capture image portions and send them to colleagues via standard messaging services for consultation.

SUMMARY

Embodiments of the present invention provide alternative devices and/or methods which allow for intuitive and easy-to-use identification of at least one medical reference image which is similar to a current examination image. Particularly, embodiments of the present invention provides alternative devices and/or methods for identification of at least one reference image which are generally compatible to existing radiology hard- and software equipment.

Embodiments of the present invention are directed to a method for identification of at least one medical reference image, a corresponding system, a corresponding computer-program product and a computer-readable storage medium. Alternative and/or preferred embodiments are object of the claims.

In the following, the technical solution according to the embodiments of the present invention is described with respect to the apparatuses as well as with respect to the methods. Features, advantages or alternative embodiments described herein can likewise be assigned to other and vice versa. In other words, claims addressing the inventive method can be improved by features described or claimed with respect to the apparatuses. In this case, e.g. functional features of the method are embodied by objective units or elements of the apparatus.

Accordingly, a first embodiment of the present invention is directed to a method for identification of at least one medical reference image, comprising:

providing a medical representation image based on a current examination image depicting a body part of a first patient;

defining a region of interest in the medical representation image;

generating a feature signature, at least for the region of interest defined in the medical representation image;

comparing the medical representation image with a plurality of medical images of at least one second patient stored in a medical image database, based on the feature signature generated; and identifying at least one medical image in the medical image database as the at least one medical reference image, the at least one medical reference image providing a similarity degree to the medical representation image above a threshold, wherein the generating is performed using a trained machine-learning algorithm.

According to a second embodiment, the present invention is directed to a system for identification of at least one medical reference image, comprising:

an interface adapted to
provide a medical representation image based on a current examination image representing a body part of a first patient, and at least one processor adapted to
define a region of interest in the medical representation image,
generate a feature signature at least for the region of interest in the medical representation image,
compare the medical representation image with a plurality of medical images stored in a medical image database based on the feature signature generated,
identify at least one medical image in the medical image database as the at least one medical reference image, the at least one medical reference image providing a similarity degree to the medical representation image above a threshold,
wherein the computing unit is adapted to run a trained machine-learning algorithm to generate the feature signature.

According to another embodiment, the present invention is directed to a system for identification of at least one medical reference image, comprising:

an interface adapted to
provide a medical representation image based on a current examination image representing a body part of a first patient, and
processing circuitry adapted to
define a region of interest in the medical representation image,
generate a feature signature at least for the region of interest in the medical representation image,
compare the medical representation image with a plurality of medical images stored in a medical image database based on the feature signature generated,
identify at least one medical image in the medical image database as the at least one medical reference image, the at least one medical reference image providing a similarity degree to the medical representation image above a threshold,
wherein the processing circuitry is adapted to run a trained machine-learning algorithm to generate the feature signature According to another embodiment, the present invention is directed to a non-transitory computer program product storing program elements to configure a processor of a system to identify at least one medical reference image by performing the method of an embodiment, when the program elements are loaded into a memory of the processor and executed by the processor.

According to another embodiment, the present invention is directed to a non-transitory computer-readable medium storing program elements, readable and executable by a processor of a system for identification of at least one medical reference image, to perform the method of an embodiment when the program elements are executed by the processor.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general the figures are not to scale. In the following.

DETAILED DESCRIPTION OF THE EXAMPLE EMBODIMENTS

Figure 1:
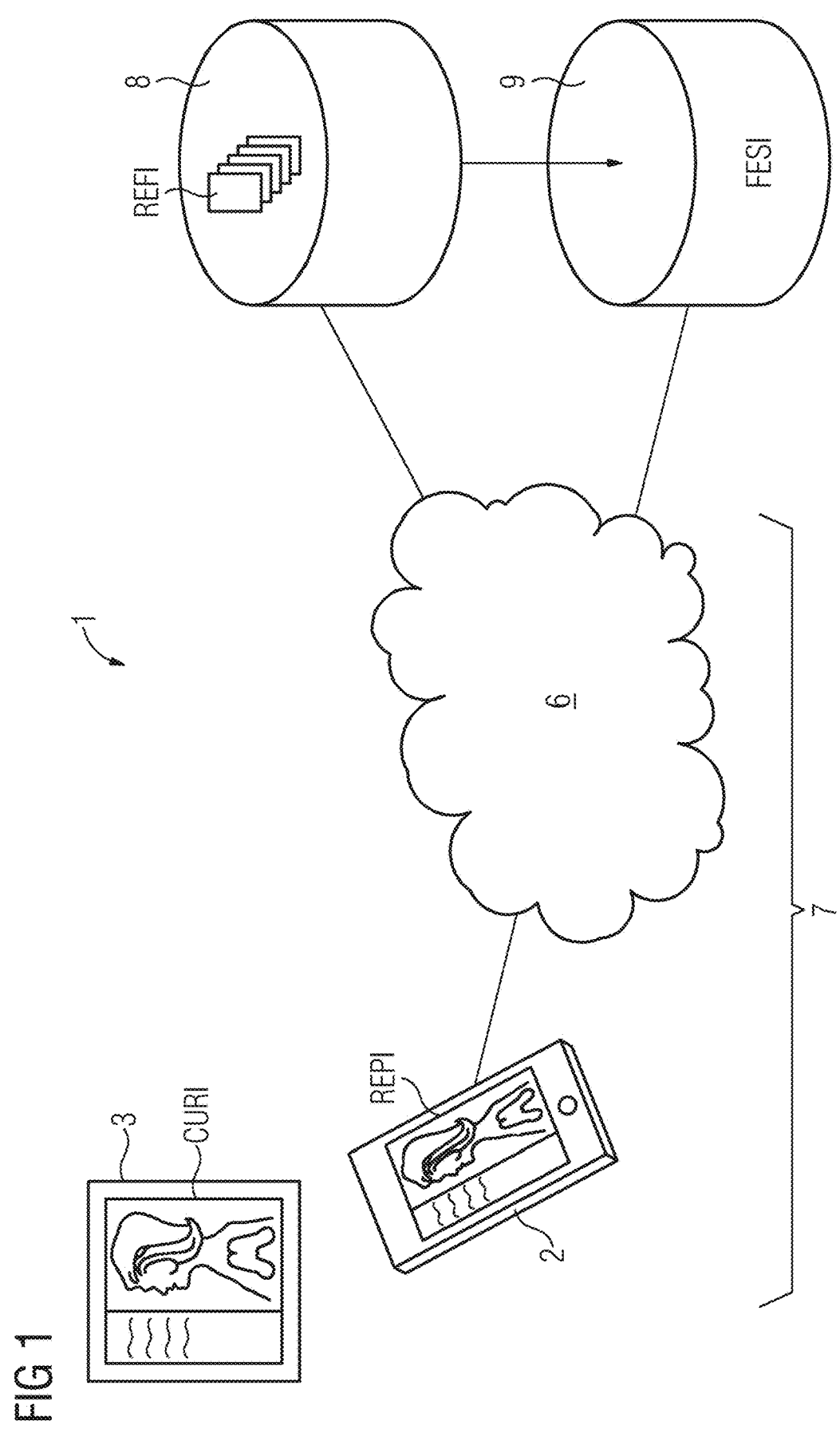
FIG. 1 depicts an inventive system for identification of at least one medical reference image according to an embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, at least one processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including at least one processor and/or processing circuitry). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, a first embodiment of the present invention is directed to a method for identification of at least one medical reference image. The method comprises numerous steps.

A first step is directed to providing a representation image based on a current examination image depicting a body part of a first patient. A second step is directed to defining a region of interest in the representation image. Another step is directed to generating a feature signature at least for the region of interest in the representation image. A further step is directed to comparing the representation image with a plurality of medical images of at least one second patient stored in a medical image database based on the generated feature signature. A further step is directed to identifying at least one medical image in the database as the medical reference image, the medical reference image providing a similarity degree to the representation image above a predefined threshold.

The step of generating is carried out using a trained machine-learning algorithm.

A current examination image is a medical image acquired using a medical imaging modality, wherein a medical imaging modality corresponds to a system used to generate or produce medical images. For example, a medical imaging apparatus may be a computed tomography system, a magnetic resonance system, an angiography (or C-arm X-ray) system, a positron-emission tomography system or the like. Correspondingly, a current examination image may be a computed tomography image, a magnetic resonance image, an angiography image, a positron-emission tomography image or the like. A current examination image is a medical image which is currently analyzed and/or evaluated and/or examined by a radiologist as regards a first patient to deduce clinical findings. The current examination image may be currently displayed on a monitor, a display screen, on a lightbox or the like arranged in a radiology department to enable a radiologist to examine the current examination image and to provide a radiology report for the first patient based on the current examination image. The current examination image may be a digital image and or an analog image, e.g. according to DICOM format or as exposed X-ray film material. The current examination image represents or depicts a body part of the first patient, which is to be understood as the patient currently under examination. The depicted body part of the first patient corresponds to a body region, a body (sub-) area, organ or tissue like abdomen, thorax, lung, neck, heart, head, leg and/or the like or at least parts of it.

The current examination image, especially in digital form, may be a two-, three or four-dimensional medical image, either providing two and/or three dimensions in space, with or without an additional dimension in time.

A representation image corresponds to a digital representation of the current examination image, i.e. a digital version of the current examination image. With other words, the representation image depicts the same body part of the first patient as the current examination image does. The representation image is however typically characterized in that it provides less image quality than the current examination image. Less image quality is preferably caused by artefacts which are introduced by generating the representation image. The artefacts may comprise less spatial resolution, less color or grey scale depth or dynamic range, image artefacts like e.g. Moiré-streaks, distortions, pixel grid patterns, illumination inhomogeneity artefacts or the like compared to the current examination image.

The representation image may be a two- or three-dimensional medical image, providing two or three dimensions in space, the two spatial dimensions being optionally equipped with an additional dimension in time. Thus, the representation image may be generated by taking a two-dimensional photograph of one current examination image or by taking numerous photographs of several current examination images depicted in a row on the radiology screen or lightbox. In case numerous current examination images are photographed, the representation image may correspond to an image stack, wherein the image stack may either comprise three spatial dimensions (three-dimensional volume) or two spatial dimensions and one time dimension (video). Here, providing the representation image may comprise a further step of image stacking.

Alternatively, the representation image may be generated by taking a digital snapshot of a current medical image depicted on a display screen using a corresponding computer program. Accordingly, a software running on the operating system of a radiology workstation could be used to acquire or capture a snapshot as a representation image. Doing so, less image artefacts are expected. The thus generated representation image does represent the current examination image, i.e. a DICOM image with original bit-depth, geometric and other acquisition parameters. The representation image may be generated according to well known graphic or video formats, such as a compressed format like JPEG, JPEG2000 or row data format or TIFF or an MPEG, AVI, MOV, FLV or RM-format.

The generated representation image is used to define a region of interest. A region of interest is to be understood as a group of image elements like pixels or voxels within the representation image. The region of interest comprises at least one, but preferably numerous image elements of the representation image. The region of interest may likewise comprise all image elements of the representation image. The region of interest may be a two- or three-dimensional region. The region of interest (ROI) represents an area or a volume within the depicted body part of the first patient, which is of specific interest for the radiologist analyzing the current examination image of the first patient. For example, the region of interest is positioned such that it comprises or covers a suspicious or atypical anatomical structure like a lesion or a calcification or the like. Preferably, the region of interest covers additional neighboring tissue representing unsuspicious areas for providing additional contextual information. A region of interest also covering not only a lesion but also surrounding tissue may later on serve for realistic Hounsfield-like grayscale normalization of the representation image or only the region of interest The region of interest may have an arbitrary shape, preferably the region of interest is of circular or quadratic form. Preferably, not only one region of interest (ROI), but two or more regions of interest are defined. For example, in case the representation image depicts more than one lesion or pathologies, they can be considered for later feature extraction with individual regions of interest.

Alternatively, the region of interest may be defined by providing the representation image. Thus, both these steps may be combined thereby reducing image data amount and necessary computational power involved in the following inventive procedure.

The representation image is then analyzed for visual characteristics. In this step a feature signature is generated for the representation image. This step of image analysis, e.g. feature extraction, may e.g. comprise identification, analysis and/or measurement of objects, local and or global structure and/or texture present in the representation image. The feature signature preferably comprises not only one, but numerous features which as a sum characterize the analyzed image. Most preferably, above mentioned image analysis is directed or better said limited to the region of interest. With other words, algorithms for image analysis are only applied to the image elements comprised in the region of interest in the representation image. However, remaining image parts of the representation image may be analyzed as well and further image features may be determined which additionally characterize the analyzed representation image.

The generated feature signature may comprise an anatomical feature and/or structure, like e.g. the presence of a landmark or the size of an organ or the structure, texture and/or density of an identified tissue or organ. The feature signature may likewise comprise a parameter characterizing a color and/or grey scale scheme or contrast characteristics or local gray scale gradients present in the analyzed image, preferably in the defined region of interest. However, the identified feature signature may further comprise a parameter indicative of information as regards the surrounding of the current examination image which may also be present in the representation image, e.g. information indicative of the reading software/application used for reading or meta data information in the form of text representations, e.g. textual overlays as patient IDs, acquisition protocol parameters, or patient specific information in general to retrieve additional information useful for retrieving similar cases.

Now, the representation image is in shape to be compared with a plurality of medical images of at least one second patient. The at least one second patient corresponds to one or a group of more patients which are other than the first patient. The plurality of medical images corresponds to a group of individual medical images each representing or depicting at least partially the same body part as the current examination image for the at least one second patient. The plurality of medical images may comprise medical images which were acquired using a medical imaging modality, like a computed tomography system, magnetic resonance tomography system, a C-arm x-ray system or the like. Preferably, the plurality of medical images comprises medical images which were acquired using the same medical imaging modality which was used for the current examination image. The current examination image and the plurality of medical images depict, comprise or show at least one common anatomical structure, organ, tissue or the like for the first and the second patient. The plurality of medical images and/or the current examination image may comprise additional or extra anatomical structures which are not present in the respective image it is compared to. With other words, the current image and the plurality of medical images may cover different or the same field of view. However, the plurality of medical images preferably comprises medical images which cover, depict or show a body part of a second patient which corresponds to or covers at least the region of interest in the representation image. The plurality of medical images may comprise two-, three- or four-dimensional images. The plurality of medical images preferably is acquired prior to the current examination image, most preferably long before the current examination image.

The plurality of medical images may thus be stored in a medical image database, which may be located on a central cloud-server which is accessible for authorized web services, or on a local hospital server like a RIS or PACS or the like.

The comparison of the images is based on the generated feature signature of the representation image.

The step of generating may thus further comprises above described image analysis which is applied to the plurality of medical images stored in the database to generate feature signatures for each of the medical images of the plurality of medical images. With other words, the inventive method applies the same image analysis algorithms to the plurality of medical images. Here, image analysis, e.g. feature extraction may likewise comprise identification, analysis and/or measurement of objects, structure and/or texture, contrast, etc. present in each of the medical images of the plurality of medical images. However, image analysis may either be applied to all image elements of each medical image or at least to image patches recognized as corresponding to the field of view of the representation image. As the current examination image may have a differing field of view compared to the plurality of medical images, similar features may be located at arbitrary positions in each of the medical images and lesions/pathologies may occur at varying positions from patient to patient, above mentioned image analysis of the plurality of medical images is applied to all image elements of the plurality of medical images. The feature signatures for the plurality of medical images preferably comprise not only one, but numerous features which as a sum characterize the analyzed image region and/or the medical image.

According to at least one embodiment of the invention, at least the step of generating a feature signature is carried out using a trained machine-learning algorithm. Preferably, the trained machine-learning algorithm comprises a neural network, most preferably a convolutional neural network. A neural net is basically built up like a biological neural net, e.g. a human brain. In particular, an artificial neural network comprises an input layer and an output layer.

It may further comprise a plurality of layers between input and output layer. Each layer comprises at least one, preferably a plurality of nodes. Each node may be understood as a biological processing unit, e.g. a neuron. With other words, each neuron corresponds to an operation applied to input data. Nodes of one layer may be interconnected by edges or connections, in particular by directed edges or connections, to nodes of other layers.

These edges or connections define the data flow between the nodes of the network. In particular, the edges or connections are equipped with a parameter, wherein the parameter is often denoted as "weight". This parameter can regulate the importance of the output of a first node to the input of a second node, wherein the first node and the second node are connected by an edge. In particular, a neural network can be trained. In particular, training of a neural network is performed based on known pairs of input and output values according to a 'supervised learning' technique, wherein the known input values are used as inputs of the neural network, and wherein the corresponding output value of the neural network is compared to the corresponding known output value.

The artificial neural network independently learns and adapts the weights for the individual nodes as long as the output values of the last network layer sufficiently correspond to the known output values according to the trainings data. For convolutional neural networks, this technique is also called 'deep learning'. The terms 'neural network' and 'artificial neural network' can be used as synonyms. Most preferably, in the training phase, the convolutional neural network is trained to identify different preferably predefined types of disease patterns such as emphysema, honey combing, and ground grass opacity. Each disease pattern may be characterized by individual visual image features. Thus, during the training phase the neural network learns to classify the extracted feature signature to at least one of these disease patterns. During training, manual mapping of individual representation images to individual disease patterns may be applied.

A first group of neural network layers may be applied to extract features from images. In this case, medical images, i.e. the gray scale and/or color values for each individual image element of the image, serve as input values for the neural network. The thus extracted features like, contrast, gradients, texture, density, or the like may be fed as input values to a second group of network layers, also known as classifiers, which serve to further assign objects and/or characteristics to at least one of the extracted features present in the image. However, both functions of the described neural network may likewise be carried out by separated, individual neural networks. With other words, image analysis for feature extraction can be carried by a first neural network, and classification, i.e. object and/or characteristic assignment can be carried out by a second neural network.

After image analysis and feature signature generation the representation image and the plurality of medical images are compared to each other. With other words, the respective feature signatures are compared to each other. For example, each individual feature contributing to the feature signature may be individually compared. Alternatively, comparison is based on a condensed feature parameter which is based on the plurality of individual features contributing to the feature signature. Preferably, this step comprises using the neuron activation value of the last but one layer of the neural network as the feature signature of the representation image. Thus, at least one medical image in the database is identified as the medical reference image based on the comparison. The medical reference image is identified or chosen according to a similarity degree to the corrected representation image, with other words based on a distance and/or difference measure of the feature signatures compared.

The predefined threshold may be set automatically and/or set by a user. The threshold may further dependent on the feature combination analyzed and/or identified in the representation image. The threshold may comprise a plurality of individual threshold values, each value belonging to an individual feature of the group of identified features and or comprise only one universal threshold value which takes into account all identified features.

Providing a representation image makes the present invention compatible to arbitrary radiology equipment. Thus not only modern advanced visualization stations may profit from the inventive automatic reference image search, but also small radiology entities with only old or outdated equipment, e.g. a light box, may apply the described inventive method. Using neural networks for image feature comparison enables a fast, i.e. basically on-the-flight search of a high number of medical images stored in a database.

According to a preferred embodiment of the present invention, the step of providing the representation image comprises acquiring a digital photograph of the current examination image. With other words, the present invention makes use of e.g. a digital camera of a mobile device like a smartphone or a tablet device. Using a digital camera a digital or analog current examination image which is depicted on a radiology monitor or a radiology lightbox is transformed into the representation image by taking a photograph of the current examination image. The inventors have realized that digital cameras are available in principle everywhere. Thus, the invention can be used widespread.

According to another preferred embodiment of the present invention, the step of defining the region of interest is based on identifying an anatomical feature in the representation image wherein the anatomical feature is indicative of a pathological condition of the patient. In this embodiment, the definition or the positioning and/or the size of the region of interest depends on anatomical features identified in the representation image.

The anatomical feature in this embodiment is characterized in that it is indicative of a pathological condition. A pathological condition comprises any anatomical deviation from a normal and/or average condition of an organ, a tissue an anatomical structure and/or only parts of it. A pathological condition may e.g. comprise atypical deformation, growth or shrinkage of an organ, atypical tissue concentrations, calcifications, cavities or lesions like cysts or nodules or the like. Furthermore, pathological condition may comprise extended textural and/or structural deviations/changes of organ tissue compared to a normal/average state.

With other words, in this embodiment, the definition of a region of interest is based on a lesion detection step. The anatomical feature indicative of a pathological condition may be detected visually by a radiologist or automatically applying a lesion detection algorithm.

According to another preferred embodiment of the present invention, the step of defining the region of interest is carried out manually by a user. This step can e.g. be realized using a user interface of the mobile device used for generating and providing the representation image. The representation may be displayed on a screen of the mobile device for region of interest definition. For this, there may be provided a graphical ROI (region of interest)-tool comprising a closed outer line, which may be superimposed to the displayed representation image and may be manipulated via touch pad of the mobile device.

Manipulation of the ROI-tool may comprise positioning within the representation image as well as changing the size and/or shape of the closed outer line to guarantee that a lesion is fully included in the thus defined region of interest. All image elements of the representation image covered by the ROI-tool belong to the region of interest for the following steps and are preferably considered for feature/object/lesion extraction and/or identification, on which the image comparison is based. Alternatively, the defining the region of interest may be carried out automatically, based on the results of a lesion detection algorithm or semi-automatically. Here, the algorithm may suggest a region of interest based on the lesion detection or based on a default setting, which may then be manually adapted.

Thus, at least one embodiment of the present invention makes sure, that the region of interest covers atypical or abnormal anatomical features. Defining a three-dimensional region of interest may comprise manually defining the region of interest in more than one image slice of a three-dimensional or video image stack. Alternatively, it may comprise manual definition in only one image slice and automatic propagation of the manually defined ROI to the remaining image slices, wherein the automatic propagation may be based on at least one detected object, preferably an object identified as lesion comprised in the manually defined region of interest.

According to an alternative embodiment, the region of interest is defined by the field of view of the representation image as defined when acquiring the digital photograph.

Artefact correction of the representation image may comprise well known techniques of image processing, like e.g.
 image segmentation,
 image registration,
 image filtering, in spatial as well as in frequency domain,
 object detection,
 object subtraction,
 whole image subtraction or (at least in parts) image overlay,
 texture, pattern and/or structure analysis and/or removal,
 contrast enhancement,
 noise reduction,
 image geometry normalization,
 image grayscale normalization and the like. The artefact correction serves to at least partially reduce or fully eliminate at least one artefact introduced to the representation image during generation. Artefact correction may be applied in two or three spatial dimensions.

According to another preferred embodiment of the present invention, the step of correcting the artefact in the representation image comprises at least the correction of one of the following artefacts: image element grid artefacts, dust artefacts, LCD refreshing artefacts, illumination artefacts and artefacts due to limited grey scale dynamic range.

As indicated earlier, taking a photograph of the current examination image to provide a representation image introduces artefacts to the representation image. When applying artefact correction algorithms, the following artefacts may preferably be reduced. Image element grid artefacts, preferably pixel grid artefacts, may originate from the current examination image being displayed with a screen or monitor providing a certain spatial resolution with an image element grid structure defined by number of image elements in x- and y-direction. The mobile device may be held in an arbitrary distance and/or angulation with respect to the screen surface which may result in spatial distortions of the depicted anatomical structures.

Other image element grid artefacts may result from defects of individual display elements of the radiology screen/monitor used to display the current examination image. Further image element grid artefacts may result from the grid structure itself which may be captured by taking a photograph. Image element grid artefacts may be corrected for e.g. using Fourier-transformations and frequency filtering techniques. Display screen as well as classical radiology light box or medical image film material may be dusty, thus leading to dust particles also represented in the representation image. These artefacts may e.g. be corrected using object detection adapted to detecting dust particles in the representation images and subtracting the detected objects from the representation image.

Furthermore, illumination of the surrounding when taking the photograph for generating the representation image may lead to color or grey scale distortions in the representation image potentially causing deviations of image contrast and/or color representation. Moiré-effects may occur in the representation image in case the digital photograph corresponds to a spatially subsampled version of the current examination image. Contrast of the representation image may further be impaired, when translating the full computed tomography and/or magnetic resonance grey scale dynamic range to rather limited dynamic range of a digital camera by taking a photograph. Of course, the list of artefacts potentially introduced to the representation image is not final, other and/or additional artefacts, e.g. increased noise level, can be considered during artefact correction as well.

In general, such artefact corrections are known and available for other image processing applications, e.g. correcting RAW images of digital cameras. Here, software programs automatically correct for optical distortions, 'vignetting'. They are also applicable for reducing noise, for image alignment or the like. Apart from that, scanned films/videos are known to be corrected to eliminate scan artefacts as dust/scratches.

According to another preferred embodiment of the present invention, the step of correcting the artefact in the representation image is carried out by a trained machine-learning algorithm, too. According to this embodiment this step may be implemented by applying a machine-learning algorithm to the artefact correction. Most preferably, artefact correction is carried out using the same neural network which is used to compare the representation image with the plurality of medical images and for identification of at least one reference image. Especially, the neural network may comprise a layer group serving to provide an artefact corrected representation image before carrying out feature extraction on the corrected representation image.

Alternatively, the artefact correction is carried out by an individual neural network which uses the original representation image as input value for the first network layer and which provides as an output value of the last network layer an artefact corrected representation image. This network may be trained using a supervised training method and providing training data comprising numerous pairs of digital photographs, i.e. representation images and the corresponding current examination images. These training data specifically account for image artefacts introduced by capturing a photograph from a monitor or a lightbox. Thus, the trained system is capable of approximating the original current examination image by applying appropriate image correction steps to the representation image. Preferably, those training data are synthetically generated by simulating addressed image artefacts.

Alternatively, real image pairs of representation image and current medical image may be used as training data. One possible approach to optimize the automatic image artefact correction to produce corrected representation images that look like the current examination images is to use 'adversarial neural networks'. One of those networks is trained to produce "natural" or "original-like" images, i.e. current examination images from screen captures, i.e. representation images, whereas the second network is trained to distinguish between 'true' current examination images and 'simulated' current examination images. These two networks compete with each other. Their training is improved iteratively. Thus, both a high quality simulator network and a high-quality discriminator network are produced.

Alternatively to the step of active artefact correction and providing an artefact corrected representation image, the 'uncorrected' representation image could be used as input for a neural network. In this case the neural network is trained to detect and/or analyze image artefacts in the representation image, however does not correct them, but compensates for them when generating corresponding feature signature. According to this alternative the step of correcting an image artefact is intrinsically accounted for by the neural network.

According to another preferred embodiment of the present invention, the steps of comparing and identifying are performed under consideration residual artefacts remaining after correcting the representation image. This embodiment advantageously takes into account that the corrected representation image may still comprise image artefacts and does not show similar image quality as original current examination images. Still, the algorithm is adapted to consider deviations in a feature signature (corresponding to a plurality of all features/objects detected and/or analyzed) of a representation image which is caused by the reduced quality during image search. This is e.g. realized by setting the predefined similarity degree threshold for comparison of the feature signatures to a lower level. Preferably, the threshold value may be set or adapted based on the identified and corrected image artefacts of a representation image.

According to another preferred embodiment of the present invention, the method further comprises acquiring an imaging parameter for the current examination image and each of the plurality of medical images, the imaging parameter being indicative of an imaging modality used for generation of the respective image, and identifying a reference image based on the identified imaging parameter. The representation image may incorporate information on the medical imaging modality used for image acquisition, e.g. the current examination image may depict in DICOM meta-data like the X-ray tube voltage representing a CT measurement. Alternatively, the representation image may comprise text or semantic information related to the image acquisition as part of the reading software used to depict the current examination image on screen. Thus, this embodiment further comprises an image analysis step further involving optical character recognition (OCR) techniques and/or semantic analysis to deduce the applied acquisition technique. By doing so, images identified as reference images may further be filtered and/or sorted based on their acquisition technique.

Alternatively, the acquisition method may be estimated based on image feature analysis, e.g. based on image type and/or image contrast and reference images may be prioritized according to their image type. Alternatively or additionally, the medical images may be analyzed for a reference anatomical location of the region of interest, e.g. by further analyzing surrounding image parts, too, and use the nearness of the anatomical locations to prioritize the reference images.

Preferably, the at least one identified reference image may be presented to a user. Preferably, the presenting is done in an order corresponding to the similarity degree between the representation image and each of the medical images. The at least one reference image is preferably presented using the screen of the mobile device also used for providing the representation image. Most preferably, in addition to the at least one reference image, further information as regards a confirmed diagnosis for the related second patient may be presented to the user when presenting the at least one reference image. By doing so, the method provides easy and fast access to expert knowledge and thus enables profound differential diagnosis for the first patient.

The further information as regards a confirmed diagnosis may e.g. comprise a list of radiological findings on which the diagnosis was based, personal information on the second patient like age, weight or gender, information on patient medical history or the like. The further information as regards a confirmed diagnosis may e.g. be extracted from a medical textbook database like 'Thieme' or may be deduced from a local medical enterprise picture archiving and communication system (PACS) and/or hospital or radiology information system (HIS/RIS).

According to a second embodiment, the present invention is directed to a system for identification of at least one medical reference image. The system comprises
an interface adapted to
provide a representation image representing a body part of a first patient, and
a computing unit (at least one processor and/or processing circuitry) adapted to
define a region of interest in the representation image,
generate a feature signature at least for the region of interest in the representation image,
compare the representation image with a plurality of medical images stored in a medical image database based on the generated feature signature,
identify at least one medical image in the database as the medical reference image, the medical reference image showing a similarity degree to the representation image above a predefined threshold,
wherein the computing unit is adapted to run a trained machine-learning algorithm for performing the step of generating.

The computing unit (at least one processor and/or processing circuitry) may optionally comprise a correction unit adapted to correct at least one artefact in the representation image prior to generating a feature signature.

The interface may be understood as a mobile device comprising a digital camera and a display screen or alternatively as the workstation including its display screen. The interface may be adapted to generate the representation image. It further comprises an interface for data exchange with a local server or a central web server via internet connection. The interface is further adapted to receive at least one reference image and/or additional information related to the second patient via the interface and to display the received information via the display screen to the user.

According to a preferred embodiment of the present invention, the system is adapted to implement the inventive method for identification of at least one medical reference image. The computing unit (at least one processor and/or processing circuitry) may comprise a definition unit adapted to define at least one region of interest. The computing unit may comprise an optional correction unit adapted to correct at least one artefact in the representation image, a generation unit adapted to generate a feature signature at least for the region of interest of the (corrected) representation image, a comparison unit adapted to compare the representation image with a plurality of medical images stored in a medical image database based on the generated feature signature, and an identification unit adapted to identify at least one medical image in the database as the medical reference image, the medical reference image showing a similarity degree to the (corrected) representation image above a predefined threshold. The computing unit is preferably adapted to run a trained machine-learning algorithm for performing the step of generating.

The computing unit can be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can be, for example, a processor system, a memory system and combinations thereof. The hardware can be configurable by the software and/or be operable by the software. Generally, all units, sub-units or modules may be at least temporarily be in data exchange with each other, e.g. via network connection or respective interfaces. Consequently, individual units may be located apart from each other, especially the definition unit may be located apart, i.e. at the mobile device, from the remaining units of the computing units.

According to another embodiment, the present invention is directed to a computer program product comprising program elements which induce a computing unit of a system for identification of at least one medical reference image to perform the steps according to the inventive method, when the program elements are loaded into a memory of the computing unit.

According to another embodiment, the present invention is directed to a computer-readable medium on which program elements are stored that are readable and executable by a computing unit of a system for identification of at least one medical reference image, in order to perform steps of the inventive method, when the program elements are executed by the computing unit.

The realization of the invention by a computer program product and/or a computer-readable medium has the advantage that already existing providing systems can be easily adopted by software updates in order to work as proposed by the invention.

The computer program product can be, for example, a computer program or comprise another element next to the computer program as such. This other element can be hardware, for example a memory device, on which the computer program is stored, a hardware key for using the computer program and the like, and/or software, for example a documentation or a software key for using the computer program. The computer program product may further comprise development material, a runtime system and/or databases or libraries. The computer program product may be distributed among several computer instances.

Summarizing, embodiments of the present invention serve to improve the assistance for radiologists in providing reference images for diagnostically proven cases looking similar to the current examination image and may further provide relevant patient specific clinical information. European patent application EP18160372.1 (the entire contents of which are hereby incorporated herein by reference), provides meaningful content for diagnostic decision support. Embodiments of the present invention however, provide this information without the need to integrate or configure the image search to the available viewing/reading software application.

Thus, embodiments of the present invention enable diagnostic support for radiologists independent of reading device, ranging from conventional light boxes (still often in use in rural areas e.g. of BRIC countries like China or Brazil) to PACS reading workstation from any vendor. Providing a solution to capture images from radiological reading displays on a mobile device and providing quick feedback with similar cases for which the diagnosis is known enables a very flexible and scalable way to provide AI based reading assistance to radiologists and clinicians.

FIG. 1 depicts a system 1 for identification of at least one medical reference image REFI according to an embodiment of the present invention. The system 1 is adapted to perform the inventive method according to one or more embodiments, e.g. as further described with reference to FIG. 3.

The system 1 comprises a mobile device 2 in form of a smartphone. The mobile device 2 comprises an interface unit in form of a digital camera with corresponding lens and optical sensor system. The system further comprises a radiology workplace screen or lightbox 3 which depicts a current examination image CURI. The mobile device 2 is adapted to take a digital photograph of the displayed current examination image CURI and thereby provides a representation image REPI.

The mobile device 2 further comprises a display for displaying the representation image and for manually defining a region of interest ROI in the representation image REPI. The mobile device 2 further comprises a processing unit 10 (including at least one processor and/or processing circuitry) adapted to execute at least one software component, e.g. in the form of a software application for serving the digital camera, for providing a graphical user interface for defining the region of interest ROI, for displaying the representation image REPI on the display and/or within the graphical user interface and/or for processing the manually input region of interest ROI together with the representation image REPI.

The system comprises a server system 6, the server system 6 comprising sub-units adapted to correct at least one artefact in the representation image REPI, to generate a feature signature FESI at least for the region of interest ROI of the corrected representation image REPI, to compare the representation image REPI with a plurality of medical images MEDI based on the generated feature signature FESI, and to identify at least one medical image MEDI as the medical reference image REFI, the medical reference image REFI showing a similarity degree to the corrected representation image REPI above a predefined threshold.

Figure 4:
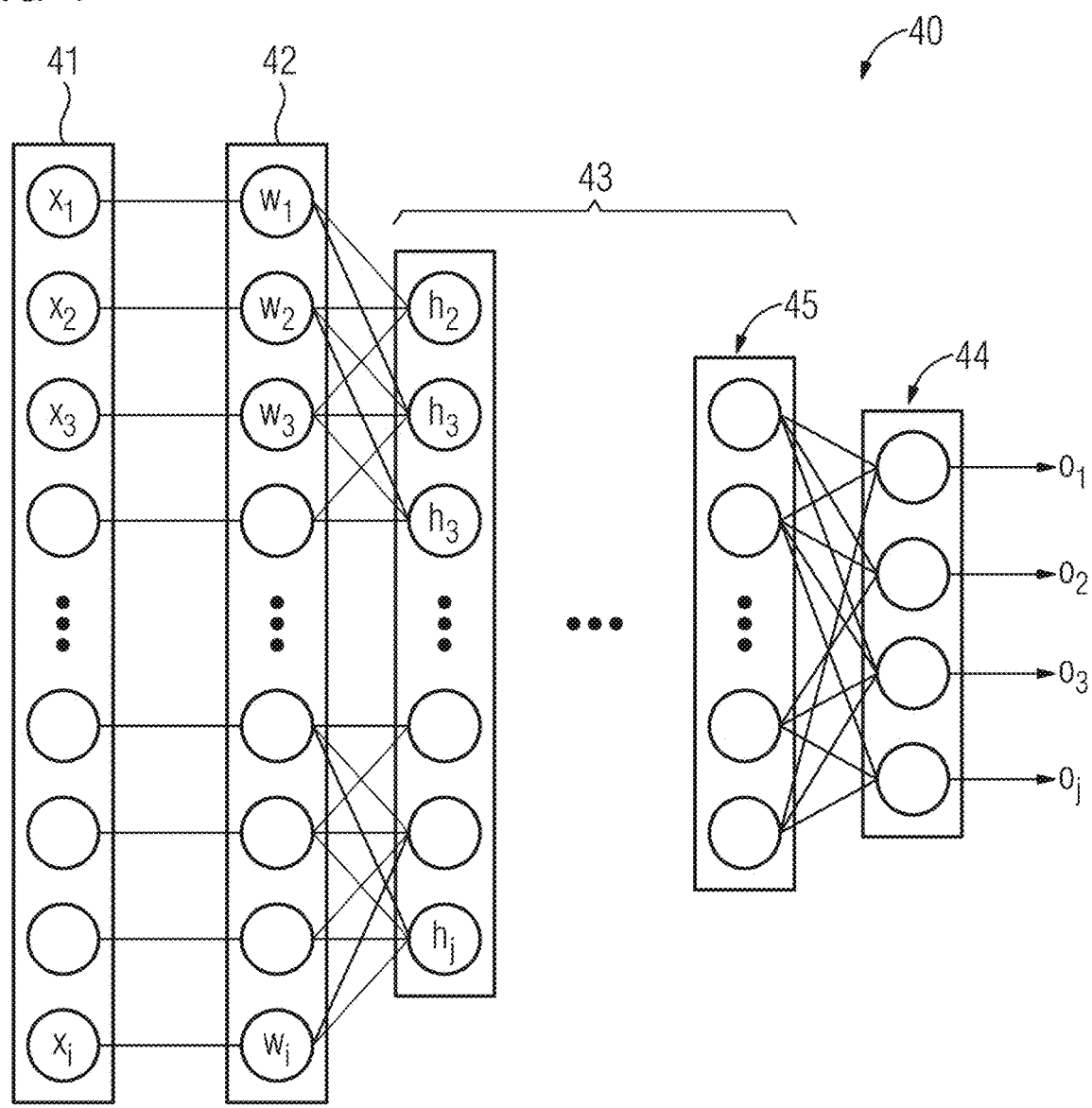
FIG. 4 depicts a neural network which may be applied in at least one embodiment of the present invention.

The server system 6 is adapted to run a trained machine-learning algorithm at least for performing the step of generating as further described with respect to FIG. 4. Server system 6 and mobile device 2 together comprise the inventive computing unit 7 (including at least one processor and/or processing circuitry) as further described in detail with respect to FIG. 2. The system 1 further comprises a database 8 for storage of the plurality of medical images MEDI. Here, more than 500.000 medical images MEDI may be stored. Database 8 may be realized as a cloud storage.

Alternatively, database 8 may be realized as a local or spread storage, e.g. a PACS (Picture Archiving and Communication System). The system 1 optionally comprises a further database 9 for storing feature signatures FESI for the plurality of medical images MEDI, i.e. more than 500.000 pre-processed feature signatures may be stored here. Medical images MEDI in database 8 and feature signatures FESI in database 9 may e.g. be interconnected via reference tags so that each feature signature FESI is unambiguously related to one medical image MEDI.

Databases 8 and 9 may likewise be combined in one database comprising both image data and respective feature data. Medical images MEDI in the database 8 may be updated continuously, e.g. on a daily or weekly basis, e.g. by the database provider like medical textbook provider 'Thieme'. In parallel, database 9 may be updated with new feature signatures FESI as soon as new medical images MEDI are integrated into database 8. Database 8 may further store further clinical information related to the medical images MEDI, wherein the clinical information may comprise e.g. related medical findings, personal information related to the at least one second patient, patient history information or the like. Alternatively a further database (not shown) may store these medical image related information.

The server system 6 may comprise either a computer/processing unit, a micro-controller or an integrated circuit. Alternatively, the server system 6 may comprise a real or virtual group of computers like a so called 'cluster' or 'cloud'. The server system may be a central server, e.g. a cloud server, or a local server, e.g. located on a hospital or radiology site.

Individual components of an embodiment of the inventive system 1 may be at least temporarily connected to each other for data transfer and/or exchange. Mobile device 2 communicates with server system 6 via interfaces to transfer e.g. a representation image REPI, the defined region of interest ROI for further processing or identified reference images REFI and optionally related clinical information for presentation on the mobile device 2. For example, server system 6 may be activated on a request-base, wherein the request is sent by the mobile device 2. Server system 6 further communicates with database 8 and 9 via interfaces. Here, feature signatures FESI of medical images are retrieved for comparison and/or medical reference images REFI and optionally related clinical information is retrieved upon identification of medical reference images REFI. Databases 8 or 9 may likewise be activated on a request-base, wherein the request is sent by the server system 6.

An interface for data exchange may be realized as hardware- or software-interface, e.g. a PCI-bus, USB or firewire.

A computing or processing unit may comprise a hardware or software component e.g. a micro-processor or a FPGA ('Field Programmable Gate Array'). A storage unit e.g. a database may be realized as Random Access Memory (RAM), as durable mass storage (hard drive, solid state disk or the like.

Data transfer preferably is realized using a network connection. The network may be realized as local area network (LAN), e.g. an intranet or a wide area network (WAN). Network connection is preferably wireless, e.g. as wireless LAN (WLAN or WiFi). The network may comprise a combination of different network examples.

Figure 2:
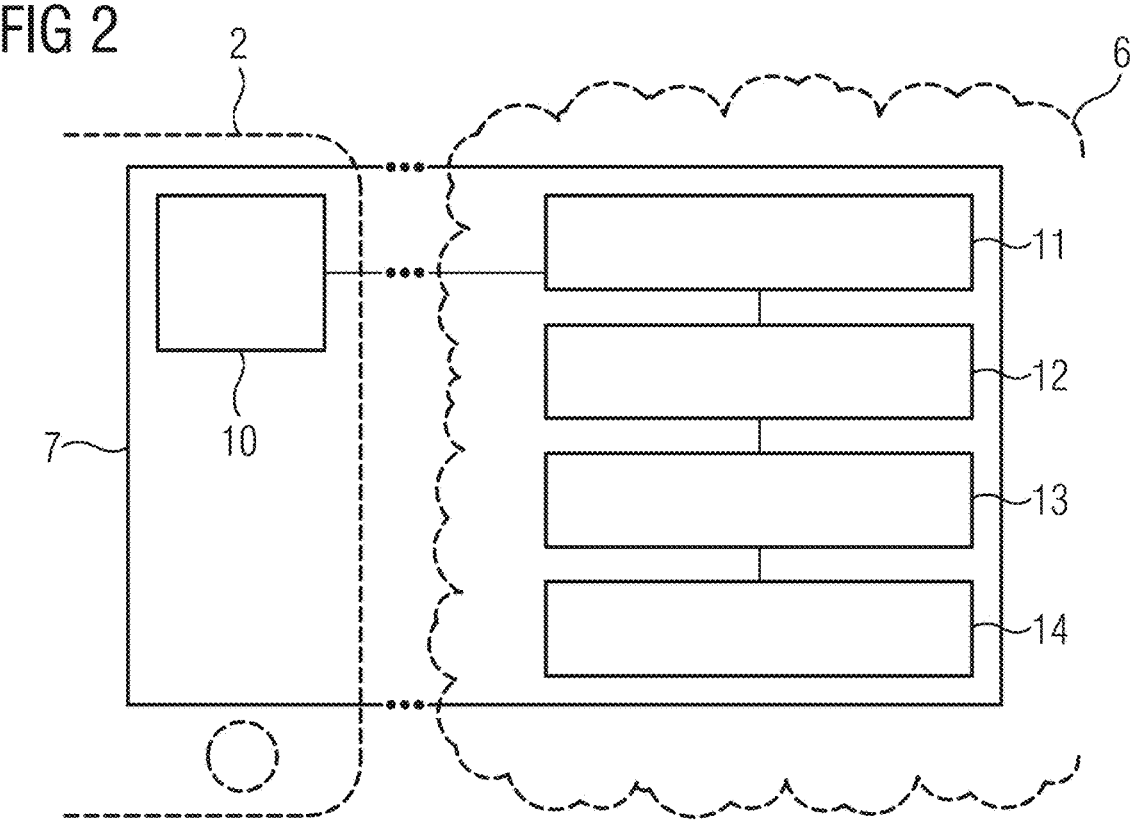
FIG. 2 depicts an inventive computing unit (at least one processor or processing circuitry) for identification of at least one medical reference image according to an embodiment of the present invention.

FIG. 2 depicts an inventive computing unit 7 for identification of at least one medical reference image REFI according to an embodiment of the present invention. The computing unit comprises a processing unit 10. Processing unit 10 is located or better said part of the mobile device 2. Processing unit 10 is arranged to execute a software application for serving the digital camera, for providing a graphical user interface for defining the region of interest ROI, for displaying the representation image REPI on the display and/or within the graphical user interface and/or for processing the manually input region of interest ROI together with the representation image REPI and for communicating them to the server system for further processing. The User may activate the software application via the graphical user interface and may acquire the software application e.g. by downloading it from an internet application store.

An embodiment of the inventive computing unit 7 further comprises individual computing (sub-) units 11, 12, 13, and 14. Sub-unit 11 is adapted to process the received representation image REPI for correcting at least one artefact. Sub-unit 11 may be arranged to execute or run a trained machine-learning algorithm for performing the step of correcting the representation image REPI. Sub-unit 12 is adapted to process the corrected representation image REPI to generate a feature signature FESI at least for the region of interest ROI in the corrected representation image REPI, alternatively for the whole representation image REPI.

Sub-unit 12 may also be adapted to generate in the same manner feature signatures for the plurality of medical images MEDI stores in database 8. Therefore, sub-unit 12 is especially adapted to execute or run a trained machine-learning algorithm for performing the step of generating the feature signature FESI. Sub-unit 13 is adapted to compare the representation image REPI with a plurality of medical images MEDI stored in a medical image database 8 based on the generated feature signature FESI. Sub-unit 14 is adapted to identify at least one medical image MEDI in the database 8 as the medical reference image REFI, the medical reference image REFI showing a similarity degree to the corrected representation image REPI above a predefined threshold.

Each sub-unit of the inventive computing unit 7 may be realized as individual sub-unit or sub-units may be realized as physically integrated sub-units, e.g. sub-unit 13 and 14 may be realized as only one integral comparing and identifying sub-unit. Each sub-unit may be individually connected to other sub-units and or other components of the inventive system 1 as already described with respect to FIG. 1, where data exchange is needed to perform the inventive method. For example, sub-unit 13, 14 may be connected to database 8 and/or 9 for retrieval of feature signatures FESI of the plurality of medical images MEDI or for retrieval of medical images MEDI identified as reference images REFI.

Figure 3:
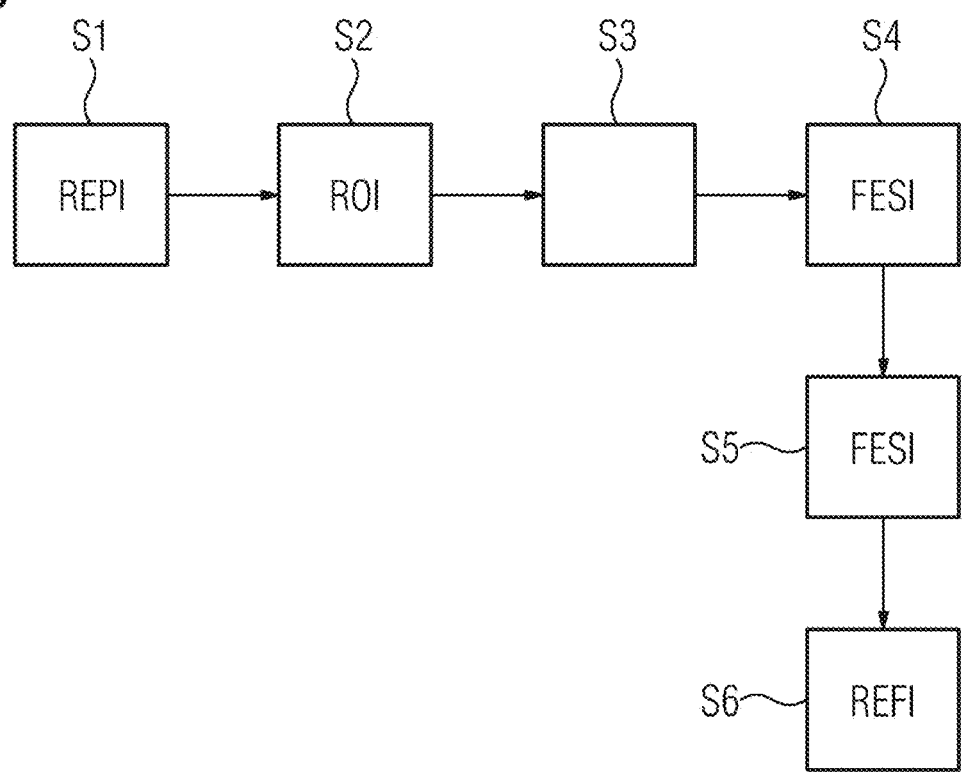
FIG. 3 depicts an inventive method for identification of at least one medical reference image according to an embodiment of the present invention.

FIG. 3 depicts an inventive method for identification of at least one medical reference image according to an embodiment of the present invention. The method comprises several steps. The order of the steps does not necessarily correspond to the numbering of the steps, but may also vary between different embodiments of the present invention.

A first step S1 is directed to providing a medical representation image REPI based on a current examination image CURI depicting a body part of a first patient. The representation image REPI is characterized in that it provides a significantly lower image quality compared to the current examination image CURI. The representation image REPI may be provided by acquiring a digital photograph of the current medical image CURI using a digital camera of a mobile device.

In case, the current medical image is a digital image displayed on a screen of a radiology monitor the representation image may further comprise visual information regarding the reading software used to display the current examination image and further used for image analysis, i.e. some color information regarding the of the application interface or some text information as regards the examined/the first patient and or information as regards the acquisition method used for the current examination image. This information may also be extracted to contribute to the feature signature FESI generated later on. The image quality of the representation image REPI is reduced due to artefacts introduced during taking the photograph.

Possible artefacts may be either of the group of less spatial resolution, less color or grey scale depth or dynamic range, image artefacts like e.g. Moiré-streaks, distortions, pixel grid patterns, illumination inhomogeneity artefacts or the like or a combination thereof. Quality of the representation image REPI is thus lowered compared to the current examination image CURI. The step of providing is not limited to the generation or the acquisition of the representation image, but may further comprise the display of the representation image REPI and/or the transferal of the reference image REPI to system components other involved in the inventive method other than the mobile device 2.

A second step S2 is directed to defining a region of interest ROI in the representation image REPI. The defining of the region of interest is carried out manually by a user or may alternatively be conducted automatically or semi-automatically. Manual and semi-automatical definition of the region of interest ROI comprise display of the representation image REPI via a graphical user interface, preferably of the mobile device 2. The user may e.g. position a region of interest tool visualized for the user as overlay to the displayed representation image REPI, further including optional adaptation of size and/or shape of the tool.

The defining the region of interest ROI is based on identifying an anatomical feature in the representation image wherein the anatomical feature is indicative of a pathological condition of the patient. With other words, the position, size and shape of the region of interest preferably depend on an abnormal or atypical feature present in the representation image. The abnormal feature may correspond to any deviation of an anatomical structure, organ or tissue like lung, heart, vessels, brain, e.g. increased or lowered local tissue density, cysts, calcifications or the like. The atypical anatomical features thus represent a pathological condition of the first patient. The anatomical feature may either be visually inspected or identified by the radiologist or may be result of a feature extraction and/or object detection step optionally comprised in this step S2. Thus, step S2 may be performed at least partially either on the mobile device 2 or on the server system 6. Corresponding data exchange is included in this step where necessary.

A third step S3 is directed to correcting at least one artefact in the representation image REPI. The artefacts as listed above are corrected in this step, i.e. image element grid artefacts, dust artefacts, LCD refreshing artefacts (in case the representation image REPI is three-dimensional comprising one time dimension), illumination artefacts and artefacts due to limited grey scale dynamic range of the digital camera.

Artefact correction may comprise image segmentation, image registration or mapping to well known anatomical atlases, image filtering, in spatial as well as in frequency domain, object detection, object subtraction, whole image subtraction or image overlay, local and/or global texture, pattern and/or structure analysis and/or removal, contrast enhancement, noise reduction or the like. Preferably, the whole representation image REPI is artefact corrected, even when only the image element values of the region of interest ROI are further processed later on. Alternatively, artefact correction is only applied to the region of interest ROI. The artefact correction serves to at least partially reduce or fully eliminate at least one artefact. Step S3 is preferably executed on the server system 6. The corrected representation image may be transferred back to the mobile device 2 for display and/or manual confirmation (in case the artefact correction provided sufficient image quality) or discarding (in case the artefact correction did not sufficiently improve image quality) by the radiologist. At this juncture, the inventive method may start anew by providing another representation image according to step S1. Alternatively, the step may comprise providing an optical and/or acoustical warning message to the user via the mobile device that representation image REPI quality is insufficient and that acquisition of a new representation image REPI is suggested- Preferably, the correcting the artefact in the representation image is carried out by a trained machine-learning algorithm, e.g. a neural network 40 as will be described in further detail with respect to FIG. 5.

A fourth step S4 is directed to generating a feature signature FESI at least for the region of interest ROI defined in the corrected representation image REPI. This step is performed using a trained machine-learning algorithm, preferably a neural network 40 as will be described in further detail with respect to FIG. 5. Step S5 is preferably performed on the server system 6 of the inventive system 1. Most preferably, steps S3 and S4 are performed by the same neural network. Feature signature FESI of the representation image REPI is preferably represented by the output values of the last but one layer 45 of the neural network 40. Thus, the neural network performs 40 at least one, preferably more of the following operations on the representation image REPI: identification, analysis and/or measurement of objects, local and/or global structure and/or texture analysis.

The feature signature FESI thus preferably comprises numerous features which as a sum characterize the analyzed image. Image analysis may preferably limited to the region of interest ROI defined for the representation image REPI. However, remaining image parts of the representation image REPI may be analyzed as well and further image features may be determined which additionally characterize the representation image REPI. The generated feature signature FESI may thus comprise landmark information or size/diameter of organs, structural, textural and/or density parameters for identified tissue and/or organ.

The feature signature FESI may likewise comprise a parameter characterizing a color and/or grey scale scheme or contrast characteristics or local gray scale gradients present in the analyzed image, preferably in the defined region of interest. However, the generated feature signature FESI may further comprise a parameter indicative of information as regards the surrounding of a current examination image CURI, e.g. a parameter indicative of the reading software/application used for image reading or a parameter indicative of a imaging modality information in the form of text representations.

Accordingly, the step S4 may further comprise acquiring an imaging parameter for the current examination image CURI and each of the plurality of medical images MEDI, the imaging parameter being indicative of an imaging modality used for generation of the respective image. And incorporate this information in the feature signature FESI. Thus, Step S4 may further comprise image analysis involving optical character recognition (OCR) techniques and/or semantic analysis to deduce the applied acquisition technique.

Optionally, the step S4 may comprise feature signature FESI generation for each of the plurality of medical images stored in database 8 and storing the feature signatures FESI in database 9. Preferably, this step may be performed upstream the inventive method steps to reduce performance time upon requesting the display of reference images REFI.

A fifth step S5 is directed to comparing the artefact corrected representation image REPI with a plurality of medical images MEDI of at least one second patient stored in a medical image database 8 based on the generated feature signature FESI. Preferably, this step comprises using the output value of the last but one layer of the neural network as the feature signature FESI of the representation image REPI. This feature signature FESI is compared with feature signatures FESI of a plurality of medical images MEDI as pre-stored e.g. in database 9.

The feature signatures FESI of the plurality of images may correspond to feature signatures FESI for whole medical images or only for image patches corresponding to only parts of the medical images MEDI. The feature signatures FESI of the medical images MEDI in the database 8 are assigned with clinically confirmed disease patterns corresponding to defined feature patterns for e.g. honey combing, ground glass opacity or emphysema for lung tissue. Thus the representation image REPI can be analyzed against several confirmed diagnosis based on the extracted features. This step comprises data exchange at least between the server system 6 and the database 9.

A sixth step S6 is directed to identifying at least one medical image MEDI in the database 8 as the medical reference image REFI, the medical reference image REFI providing a similarity degree to the corrected representation image REPI above a predefined threshold. The similarity degree to the corrected representation image REPI is preferably calculated using a distance and/or difference measure of the feature signatures FESI compared, preferably the Euclidian distance. All medical images MEDI with a feature signature FESI sufficiently similar is identified as a reference image REFI. The predefined threshold for sufficient similarity is set automatically and/or set by a user. The threshold value may preferably depend on the predefined feature combination of a disease pattern. The threshold value may be in the form of a relative or absolute difference.

An embodiment of the inventive method advantageously comprises consideration of residual artefacts remaining after correcting the representation image REPI for the steps of comparing (S5) and identifying (S6). This advantageously takes into account residual image artefacts in the corrected representation image REPI. Thus, the algorithm is adapted to consider during similar image search deviations in feature signature FESI of a representation image REPI which is due to the reduced image quality. This is e.g. realized by setting the predefined similarity degree threshold for comparison of the feature signatures to a lower level. Preferably, the threshold value may be set or adapted based on the identified and corrected image artefacts of a representation image.

Optionally, an embodiment of the inventive method may comprise a further step for presentation of at least one identified reference image REFI to a user. Preferably, the presenting is done in an order corresponding to the similarity degree between the representation image REPI and each of the reference images REFI images. Presentation is preferably performed on the screen of the mobile device 2. Accordingly, this step comprises data transfer, between server system 6, database 8 and mobile device 2.

Most preferably, in addition to the at least one reference image REFI, further information as regards a confirmed diagnosis for the related second patient may be presented to the user in parallel to the at least one reference image REFI. By doing so, the method provides easy and fast access to expert knowledge and thus enables profound differential diagnosis for the first patient.

FIG. 4 depicts a neural network 40 according to an embodiment of the present invention as is may be used for performing the inventive method according to FIG. 3. The neural network 40 answers to input values of a plurality of input nodes xi of an input layer 41. All nodes of the neural network 40 are applied to generate one or a plurality of output values $o_j$. The neural net 40 of this embodiment learns by adapting weights or weighting parameters $w_i$ (weights) of individual nodes based on training data. Input values for the input nodes $x_i$ are image element values, preferably pixel values, of a corrected representation image REPI.

Most preferably, only the image element values corresponding to the defined region of interest ROI are fed to the input layer 41. Alternatively, more than the image element values of the region of interest ROI are used as input. Alternatively, in case the neural network 40 is further adapted to perform the step of artefact correcting the representation image REPI, image element values of the original, i.e. uncorrected representation image REPI may be fed to the input layer 41. The neural network 40 weights 42 the input values based on a learning procedure. Output values $o_j$ of the output layer 44 of the neural network 40 may preferably correspond to identification and/or confirmation of a disease pattern recognized in the representation image. For example, the output layer 44 may comprise four output nodes, each of the four nodes representing a disease pattern out of four disease patterns.

A disease pattern is to be understood as a predefined and preferably clinically confirmed visual image feature combination. With other words, output value $o_1$ may be representative of a first disease, output value $o_2$ may be representative of a second disease, output value $o_3$ may be representative of a third disease, and output value $o_j$ may be representative of a fourth disease. According to a preferred embodiment, the representation image REPI depicts at least partially the lung of a first patient, e.g. the representation image REPI corresponds to a lung/thorax computed tomography image. Potential output values $o_j$ according to predefined disease patterns may e.g. comprise 'honey combing', 'ground glass opacity', emphysema or the like. According to this embodiment, the neural network 40 is trained during training phase using training data in the form of labeled image samples for the four different disease patterns. The labeling of the training data is preferably conducted manually in advance.

The artificial neural network 40 further comprises a hidden layer 43 each comprising a plurality of nodes $h_j$. There may be more than one hidden layers 43, wherein the output values of one hidden layer serve as input values for the following hidden layer. The individual nodes of a hidden layer 43 execute mathematical operations. Thus, an output value $h_j$ of a node corresponds to a non-linear function f of its input values $x_i$ and the weighting parameters $w_i$. After receiving an input value $x_i$, the node $h_j$ may for example execute a summation of a multiplication of each input value $x_i$ wherein the multiplication is weighted with the weighting parameter $w_i$, as defined below:

$$h_j = f(\Sigma x_i \cdot w_{ij})$$

Most preferably, an output value of a node $h_j$ is generated as a function f of node activation, e.g. a sigmoidal function or a linear ramping function. The output values $h_j$ are thus propagated through the hidden layers 43 and finally transferred to the output layer 44. Here, once again, summation of a weighted multiplication of each output value $h_j$ may be calculated as a function of node activation f:

$$o_j = f(\Sigma h_i \cdot w'_{ij})$$

Most preferably, the hidden layers 43 comprise a last hidden layer 45 corresponding to the last but one layer of the neural network 40. Most preferably, the sum of output values $h_j$ of the last hidden layer 45 is used as the feature signature of the representation image REPI for medical image MEDI search.

The shown neural network 40 corresponds to a feedforward neural network. Accordingly, all nodes $h_j$ of the networks layers 42, 43, 44, 45 process the output values of the previous layer in the form of their weighted sum as input values. Of course, other embodiments of neural network types may be applied, e.g. a feedback-network, wherein an input value of a node of one layer may be the output value of a node of a consecutive network layer.

The neural net 40 may preferably be trained to recognize disease patterns using a method according to supervised learning. Well established is the backpropagation method, which may be applied for all embodiments of the present invention. During training phase the neural network 40 is applied to training input values to produce corresponding and known output values. Mean square error (MSE) between produced and expected output values are calculated in an iterative manner to adapt individual weighting parameters $w_i$ as long as deviation between calculated and expected output values is within predefined tolerance.

Wherever meaningful, individual embodiments or their individual embodiments and features can be combined or exchanged with one another without limiting or widening the scope of the present invention. Advantages which are described with respect to one embodiment of the present invention are, wherever applicable, also advantageous to other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for identification of at least one medical reference image, the method comprising:
    obtaining a medical representation image based on a current examination image depicting a body part of a first patient, the medical representation image having a lower quality relative to the current examination image;
    defining a region of interest in the medical representation image;
    generating a feature signature at least for the region of interest defined in the medical representation image;
    comparing, based on the feature signature, the medical representation image with a plurality of medical images of at least one second patient, the plurality of medical images stored in a medical image database; and
    identifying at least one of the plurality of medical images as the at least one medical reference image, the at least one medical reference image providing a similarity degree to the medical representation image that is above a threshold, wherein
        the generating a feature signature is performed using a trained machine-learning algorithm.

2. The method of claim 1, wherein the obtaining a medical representation image comprises:
    acquiring a digital photograph of the current examination image.

3. The method of claim 2, wherein the defining a region of interest comprises:
    defining the region of interest based on an identified anatomical feature in the medical representation image, and wherein
    the identified anatomical feature is indicative of a pathological condition of the first patient.

4. The method of claim 2, further comprising:
    correcting at least one artefact in the medical representation image before generating the feature signature.

5. The method of claim 4, wherein the at least one artefact includes at least one of an image element grid artefact, a dust artefact, a LCD refreshing artefact, an illumination artefact or an artefact due to limited grey scale dynamic range.

6. The method of claim 4, wherein the correcting at least one artefact in the medical representation image is carried out by a trained machine-learning algorithm.

7. The method of claim 1, wherein the defining a region of interest comprises:
    defining the region of interest based on an identified anatomical feature in the medical representation image, and wherein
    the identified anatomical feature is indicative of a pathological condition of the first patient.

8. The method of claim 7, wherein the defining a region of interest is carried out manually by a user.

9. The method of claim 1, wherein the defining a region of interest is carried out manually by a user.

10. The method of claim 1, further comprising:
    correcting at least one artefact in the medical representation image before generating the feature signature.

11. The method of claim 10, wherein the at least one artefact includes at least one of an image element grid artefact, a dust artefact, a LCD refreshing artefact, an illumination artefact or an artefact due to limited grey scale dynamic range.

12. The method of claim 11, wherein the correcting at least one artefact in the medical representation image is carried out by a trained machine-learning algorithm.

13. The method of claim 10, wherein the correcting at least one artefact in the medical representation image is carried out by a trained machine-learning algorithm.

14. The method of claim 13, wherein the comparing and the identifying are performed considering residual artefacts remaining after the correcting at least one artefact in the medical representation image.

15. The method of claim 10, wherein the comparing and the identifying are performed considering residual artefacts remaining after correcting the at least one artefact in the medical representation image.

16. The method of claim 1, further comprising
    acquiring a first imaging parameter for the current examination image and acquiring a second imaging parameter for each of the plurality of medical images, the first imaging parameter and the second imaging parameter being indicative of an imaging modality used for image acquisition, and wherein
    the identifying identifies the at least one medical reference image based on at least one of the first imaging parameter or the second imaging parameter.

17. A non-transitory computer program product storing program elements to configure a processor of a system to identify at least one medical reference image by performing the method of claim 1, when the program elements are loaded into a memory of the processor and executed by the processor.

18. A non-transitory computer-readable medium storing program elements, readable and executable by a processor of a system for identification of at least one medical reference image, to perform the method of claim 1 when the program elements are executed by the processor.

19. A system for identification of at least one medical reference image, the system comprising:
    an interface adapted to obtain a medical representation image based on a current examination image representing a body part of a first patient, the medical representation image having a lower quality relative to the current examination image; and
    at least one processor adapted to
        define a region of interest in the medical representation image,
        generate a feature signature at least for the region of interest in the medical representation image, compare, based on the feature signature, the medical representation image with a plurality of medical images of at least one second patient, the plurality of medical images stored in a medical image database, identify at least one of the plurality of medical images as the at least one medical reference image, the at least one medical reference image providing a similarity degree to the medical representation image that is above a threshold, wherein the at least one processor is adapted to run a trained machine-learning algorithm to generate the feature signature.

20. The system of claim 19, wherein the at least one processor is adapted to correct at least one artefact in the medical representation image.

21. The system of claim 19, wherein the medical representation image is a digital photograph of the current examination image.

22. A system for identification of at least one medical reference image, the system comprising:

an interface adapted to obtain a medical representation image based on a current examination image representing a body part of a first patient, the medical representation image having a lower quality relative to the current examination image and processing circuitry adapted to define a region of interest in the medical representation image, generate a feature signature at least for the region of interest in the medical representation image, compare, based on the feature signature, the medical representation image with a plurality of medical images stored in a medical image database, identify at least one of the plurality of medical images as the at least one medical reference image, the at least one medical reference image providing a similarity degree to the medical representation image that is above a threshold, wherein the processing circuitry is adapted to run a trained machine-learning algorithm to generate the feature signature.

23. The system of claim 22, wherein the processing circuitry includes a field programmable gate array.

24. The system of claim 22, wherein the processing circuitry is adapted to correct at least one artefact in the medical representation image.

25. The system of claim 22, wherein the medical representation image is a digital photograph of the current examination image.

* * * * *